(12) United States Patent
Merimon et al.

(10) Patent No.: US 8,735,139 B2
(45) Date of Patent: May 27, 2014

(54) SYSTEM AND METHOD FOR CONTINUOUS FERMENTATION OF ALGAE

(75) Inventors: Tommie Merimon, Houston, TX (US); Jerry McCall, Houston, TX (US)

(73) Assignee: Missing Link Technology, LLC, Houston, TX (US)

( * ) Notice: Subject to any disclaimer, the term of this patent is extended or adjusted under 35 U.S.C. 154(b) by 155 days.

(21) Appl. No.: 13/299,844

(22) Filed: Nov. 18, 2011

(65) Prior Publication Data

US 2012/0064617 A1    Mar. 15, 2012

Related U.S. Application Data

(62) Division of application No. 12/348,078, filed on Jan. 2, 2009.

(60) Provisional application No. 61/018,620, filed on Jan. 2, 2008.

(51) Int. Cl.
  *C12N 1/12*      (2006.01)
  *C12Q 1/68*      (2006.01)

(52) U.S. Cl.
  USPC .................................... 435/257.1; 435/6.1

(58) Field of Classification Search
  None
  See application file for complete search history.

*Primary Examiner* — Annie-Marie Falk
(74) *Attorney, Agent, or Firm* — Egbert Law Offices, PLLC

(57) ABSTRACT

The present invention is a method for fermentation of algae or algaefaction method. The method includes feeding a hydrocarbon composition into a gasifier and pre-heating a biomass stream from a fermentation reactor. The biomass stream includes a liquid portion, a catalyst, and a biomass solids portion ranging between 15-92% by weight of the biomass stream. The biomass solids portion is algae or algal solids. The biomass stream is pre-heated to a temperature range between 200° F. and 500° F. Both the syngas and the pre-heated biomass stream are injected as a mixture into a reactor, where the mixture is separated into a gas component, liquid component, and solids component. The solids component is algal crude, which can be collected for processing as transportation fuels. The gas component is a lower temperature syngas, which can also be collected for processing as electricity or transportation fuels.

5 Claims, 2 Drawing Sheets

US 8,735,139 B2

SYSTEM AND METHOD FOR CONTINUOUS FERMENTATION OF ALGAE

RELATED U.S. APPLICATIONS

The present invention claims divisional priority from application Ser. No. 12/348,078, filed on Jan. 2, 2009, entitled "SYSTEM AND METHOD FOR CONTINUOUS FERMENTATION OF ALGAE", presently pending. Application Ser. No. 12/348,078 claims provisional priority from Provisional Patent Application No. 61/018,620, filed on Jan. 2, 2008.

STATEMENT REGARDING FEDERALLY SPONSORED RESEARCH OR DEVELOPMENT

Not applicable.

REFERENCE TO MICROFICHE APPENDIX

Not applicable.

BACKGROUND OF THE INVENTION

1. Field of the Invention

The present invention relates to systems for fermentation. More particularly, the present invention relates to systems of fermentation that are continuous and stirred. The present invention also relates to systems for fermentation using algae as the microorganism.

2. Description of Related Art Including Information Disclosed Under 37 CFR 1.97 and 37 CFR 1.98.

From the simplest to the most complex, biological processes maybe classified as fermentation, elementary physiological processes, and the action of living organisms. Fermentation is a biological reaction whereby a raw organic material is converted into a product by the action of microorganisms or by the action of enzymes produced by microorganisms. In a typical fermentation reaction, a raw organic material is fed into a reactor. The raw organic material can be any carbon-based material including, but not limited to, carbon dioxide, sugar products, sewage sludge, animal manures and cellulosic materials. Once in the reactor, the raw organic material is mixed with microorganisms or microbes that are suitably chosen for a desired reaction with the raw organic material. The group of microorganisms or microbes includes, but is not limited to, yeasts, bacteria, algae, molds, and protozoa.

A reaction occurs whereby a product is formed by mixing the raw organic material with the microorganisms. This product depends on the type of raw organic material used as well as the type of microorganisms or microbes used. The product of the fermentation reaction is typically recovered from the biomass of the reaction through various separation methods such as dewatering and floatation.

Fermentation processes are known as autocatalytic processes. The autocatalytic behavior of a fermentation process is represented by a sequence of events. First, when the raw organic material is first introduced into the fermentation reactor, there is only a small amount of catalytic microorganisms present in the reactor. Thus, the conversion of the raw organic material into product is slow, i.e., the rate of reaction is very low. However, as the concentration, or number, of microorganisms increases, the reaction rate rises, producing more microorganisms and more products. In a typical fermentation reaction, the reaction rate reaches a maximum followed by a gradual die-off of the raw organic material. At this point, there is very little raw organic material and a lot of product, so the rate eventually slows until there is no reaction.

Because of their nature, fermentation reactions are typically carried out in a batch reactor. Batch reactors involve reacting a finite amount of material from start to completion and then starting over with a new finite amount of material in the reactor. This type of reactor is in contrast to a continuous reactor that continuously reacts a continuous supply of material. Because batch processes inevitably have a reaction that ends, they have a high operating cost, high capital cost, complicated sequencing, and limited production capabilities. Thus, there is a need for systems allowing for continuous fermentation that have improved operating cost, capital cost, and production capabilities over batch operations.

In the past, various patents have issued relating to systems for continuous fermentation. For example, U.S. Pat. No. 6,599,735, issued on Jul. 29, 2003 to the Bartok et al., describes fermentation assembly comprising a vessel for culturing living cells, at least two storage flasks in fluid communication with the vessel for supply of liquids and a first transport means for transferring the liquids from the storage flasks to the vessel, individual appliances operably connected to the transport means for monitoring the supply of the contents of the storage flasks to the vessel, a harvest flask in fluid communication with the vessel and a second transport means for transferring the fermentation broth from the vessel to the harvest flask, and a device operably connected to the first transport means for controlling and maintaining a constant dilution rate in the vessel with varying rates of individual supply of liquid from the storage flasks to the vessel U.S. Pat. No. 5,688,674, issued on Nov. 18, 1997 to Choi et al., describes a metabolite, e.g., ethanol, that is continuously produced from low cost carbohydrate substrates by a process which comprises pulverizing the carbohydrate substrate, liquefying and saccharifying the pulverized substrate, continuously fermenting the lique-saccharified substrate in a fermentor equipped with a moving filter, in the presence of flocculent biological cells maintained at a concentration ranging from 90 to 160 g/l by using the moving filter and a culture medium to produce a fermentation product mixture, and recovering the desired metabolite from the fermentation product mixture.

U.S. Pat. No. 4,069,149, issued on Jan. 17, 1978 to Jackson, describes a deep-tank reactor utilized for fermentation of waste liquid or other liquid in a biological reaction resulting in a solid cellular material. The resulting solid material, which is in suspension, is initially separated from the bulk of the liquid by a gaseous flotation process, using the dissolved gas in the liquid as the source of gaseous bubbles for flotation purposes.

U.S. Pat. No. 4,286,066, issued on Aug. 25, 1981 to Butler et al., describes an apparatus for continuously fermenting a moist particulate feed and distilling the fermentation product where a pressure-locked auger forces a moist particulate feed from a hopper into a fermentation tank. Liquor is removed from the tank, and solids are separated therefrom to produce a beer which is distilled in a distillation column. A combustion engine powers the auger and the means for separating solids, and the engine exhaust surrounds an inlet section of said auger to help heat the pressurized feed therein to produce fermentable sugar within the auger, and the auger includes a section passing to the tank in heat exchange relation to the distillation column to provide heat for distillation. The column is a multistage column angled to face the sun and has an upper glass plate to allow solar radiation to enter and penetrate between the foraminous plates of the column.

Research into efficient algal-oil production is currently being done in the private sector. Using algae to produce biodiesel may be a viable method by which to produce enough fuel to eliminate the dependence upon harvesting fossil fuels from non-sustainable resources. Algae require sunlight, carbon dioxide, small amounts of micronutrients, water, and small amounts of heat to grow. Given the proper conditions, some algae can double its mass in less than twelve (12) hours of fermentation. Importantly, algae can produce a portion their biomass in the form of oil. Because the algae grows in an aqueous suspension, they are capable of producing large amounts of biomass and usable oil in either high rate algal ponds or photobioreactors. This oil can then be processed into usable fuel.

It is an object of the present invention to provide a system for fermentation using algae.

It is another object of the present invention to achieve up to 80% reduction in the operating costs of batch fermentation processes.

It is another object of the present invention to provide a reactor design that optimizes the fermentation reaction.

It is another object of the present invention to extract oil from harvested algae using an economical method.

It is yet another object of the present invention to provide an optimal reactor structure for any given set of operating conditions.

It is still another object of the present invention to provide concentrated algae for more efficient collection.

These and other objects and advantages of the present invention will become apparent from a reading of the attached specification.

BRIEF SUMMARY OF THE INVENTION

The present invention is a method for fermentation of algae. The method includes feeding a hydrocarbon composition into a gasifier, the gasifier converting the hydrocarbon composition into a syngas of a temperature range between 300° F. and 1500° F., the syngas being comprised of carbon monoxide, hydrogen and impurities.

A biomass stream is pre-heated. This biomass stream is comprised of a liquid portion, a catalyst, and a biomass solids portion ranging between 15-92% by weight of the biomass stream. The biomass solids portion is algae or algal solids. The biomass stream is pre-heated to a temperature range between 200° F. and 500° F.

Both the syngas and the pre-heated biomass stream are injected as a mixture into a reactor, where the mixture is separated into a gas component, liquid component, and solids component. The solids component is algal crude, which can be collected for processing as transportation fuels. The gas component is a lower temperature syngas, which can also be collected for processing as electricity or transportation fuels. The step of separating includes using an algaefaction reactor to heat the syngas and the pre-heated biomass stream to a temperature greater than 600° F., to dissolve the syngas into the liquid portion of the biomass stream in the reactor, to defuse the syngas into cellular structure of the biomass stream for a predetermined amount of time, and to flash the defused biomass stream mixture to change phase from liquid to vapor within the biomass cellular structure.

The components can be collected and possibly be cycled back to the early process steps. In particular, the higher temperature solids component can transfer heat energy to the biomass stream as the step of pre-heating. The cooled solids component can then be collected.

The process is continuous fermentation of algae through a reactor. The reactor can be a fermentation reactor having a first reactor section and a second reactor section. The first reactor section is a continuous stirred tank reactor and the second reactor section is a plug flow reactor. The first reactor section and the second reactor section are separated by a first baffle, the first baffle being movable within the fermentation reactor. The first reactor section has a second baffle that can be varied in size or shape so as to optimize the fermentation reaction within the first reactor section. In particular, the baffle of the second reactor position can be positioned for a residence time of up to seven days. The second reactor section can also have a dewatering means to remove water from the biomass product. The fermentation reactor supplies algal biomass for the algaefaction method of the present invention. Various other post-separation elements can be connected to the fermentation reactor or algaefaction reactor for further processing of the separated components.

The method of the present invention releases the oil from the cellular structure of algae. The oil is collected through standard acceptable methods including, but not limited to, gravity separation, mechanical separation, centrifugation, flocculation etc and may incorporate the use of demulsifiers to enhance and improve the separation times. The optimal reactor structure can be adjusted for a given set of operating conditions so that the most efficient and economical extraction can be used for a particular biomass stream of the algae.

DETAILED DESCRIPTION OF THE INVENTION

Figure 1:
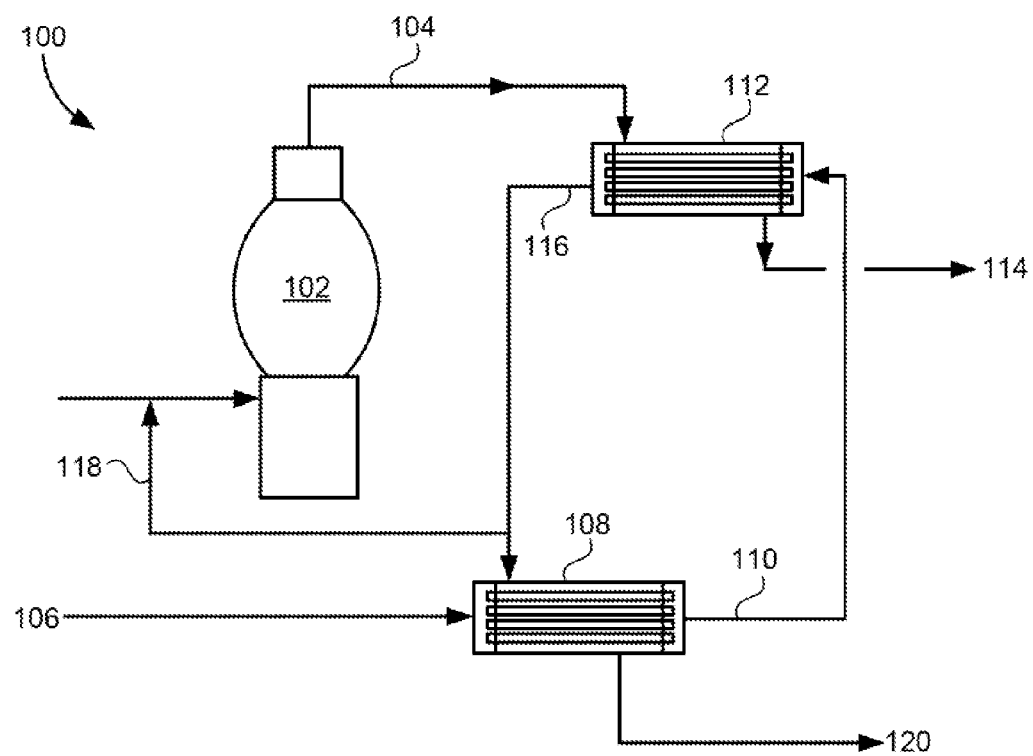
FIG. 1 is a schematic illustration of the algaefaction method for fermentation using algae of the present invention.

Referring to FIG. 1, there is the illustration of the method of the present invention for the "algaefaction" process 100 of fermenting algae and collecting the separate biological components. The algaefaction process 100 starts with feeding a hydrocarbon composition into a gasifier 102. The gasifier 102 converts the hydrocarbon composition into a syngas 104 comprised of carbon monoxide, hydrogen, and some minor impurities. The temperature of the syngas 104 ranges between 300° F. and 1500° F. A biomass stream 106, being comprised of a liquid portion, a catalyst, and a biomass solids portion is heated at a pre-heater 108. The biomass solids portion is comprised of algal solids and ranges between 15-92% by weight of the biomass stream 106. The biomass stream 106 is preferably heated to a temperature range between 200° F. and 500° F. by the pre-heater 108.

The mixture of the syngas 104 and the pre-heated biomass stream 110 is injected an "algaefaction" reactor 112. The mixture can be pressurized between 500 and 2000 psig in the algaefaction reactor. The algaefaction reactor 112 separates the mixture into a gas component, liquid component, and solids component. The solids component is algal crude 116, and the gas component is a lower temperature syngas. The lower temperature syngas 114 is collected for further processing into transportation fuel or electricity. The algal crude 116 is either cycled by to the pre-heater 108 to transfer heat energy back to the biomass stream 106 or recycled as part of the hydrocarbon composition 118 into the gasifier 102. When the algal crude 116 is cycled to the pre-heater 108, the algal crude is cooled by loss of heat to the biomass stream 106. The cooled algal crude 120 is then collected for further processing as transportation fuel.

The separation of components at the algaefaction reactor 112 includes heating the syngas 104 and the pre-heated biomass stream 110 to a temperature greater than 600° F. A temperature of 1400° F. achieves particular efficiency of this process. The syngas dissolves into the liquid portion of the biomass stream 106 in the reactor 112 and defuses into cellular structure of the biomass stream 106 for a predetermined amount of time. The defused biomass stream mixture is flashed to change phase from liquid to vapor within the biomass cellular structure in order to lysis the algal cells, releasing the components into the three separate types of components for collection. The step of flashing releases pressure in less than 0.5 sec, bursting algal cell structures.

Figure 2:
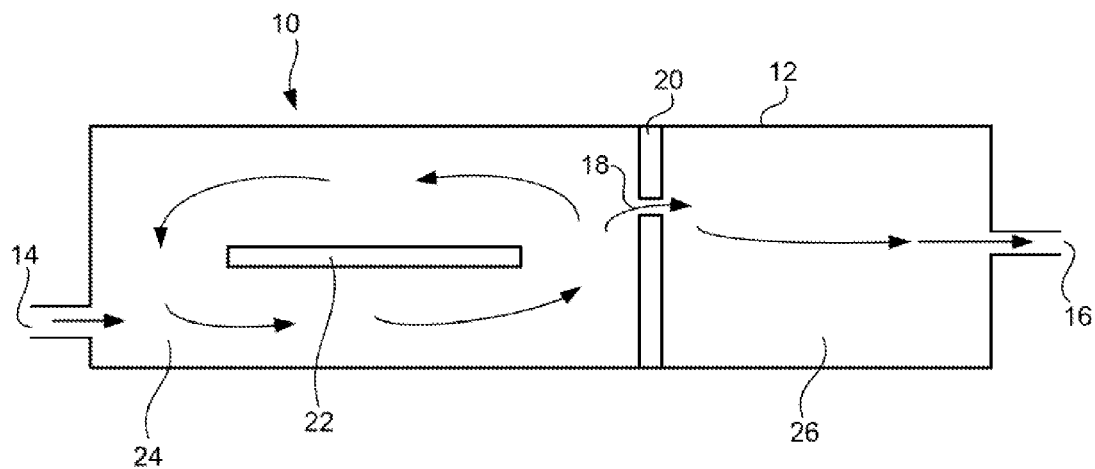
FIG. 2 is a cross-sectional view of a fermentation reactor compatible with supplying algal biomass for the method of the present invention.

The system for algaefaction process of the present invention includes the gasifier 102, the pre-heater 108, and the algaefaction reactor 112 to separate the components. Other known collections means and fluid connections between structures are also part of the claimed system. It is a further option to have a fermentation reactor, as shown in FIG. 2 as reference numeral 10, to produce the biomass stream 106 of algal biomass containing oil. This fermentation reactor 10 is part of the continuous process of the present invention, which precludes the batch processing of the prior art.

Referring to FIG. 2, there is shown a fermentation reactor tank 10 in accordance with an embodiment of the fermentation reactor of the present invention. The fermentation reactor tank 10 includes a first reactor section 24 and a second reactor section 26 separated by a baffle 20. The first reactor section 24 is a continuous stirred tank reactor, and the second reactor section 26 is a plug flow reactor. The first reactor section 24 has an inlet 14 where raw organic materials, microorganism, and recycled biomass are continuously fed. In the preferred embodiment, the microorganism is algae. The reaction in the second reactor section 26 involves transferring biomass into the plug flow reactor of the second reactor section 26 whereby the biomass converts, in the absence of light, carbohydrates into oil. This reaction increases the oil content of the biomass. This reaction occurs over a period of up to seven days. That is, the residence time of the second reactor section 26 is up to seven days.

A baffle 22 is received within the first reactor section 24 and can be varied vertically and horizontally within the first reactor section 24 so as to optimize the fermentation reaction. Baffle 20 has an opening 18 where biomass in the first reactor section 24 passes to the second reactor section 26. The second reactor section 26 has an outlet 16 where the biomass exits the fermentation reactor 10. Baffle 20 is movable along the inner walls 28 of the fermentation reactor tank 10 so as to vary the volumes of the first reactor section 24 and the second reactor section 26. Varying the volumes allows one to change the residence times in the first reactor section 24 and the second reactor section 26 so as to optimize the fermentation reaction for a raw organic material. The rate equation used to optimize the design for the fermentation reactor 10 tank is:

$$-rA = k_1 * C_c * (CA/(k_2 + CA))$$

where k1 and k2 are constants, Cc is the concentration of the microorganisms in the fermentation reactor 10, CA is the concentration of the raw organic material, and rA is the rate of reaction. This rate equation implies a shift from a "zeroeth" order rate equation at high concentrations of CA to a "first" order equation at low concentrations of CA. Therefore, the fermentation reactor tank 10 of the present invention allows for an optimal reactor design for a given set of operating conditions through manipulation of the baffles 20 and 22. In the preferred embodiment, the baffle 20 should be placed so as to have a residence time of seven days in the second reactor section 26.

The algaefaction process of the present invention is a significant development in the field of fermentation and biofuels. The algaefaction process allows continuous processing of a biomass stream from a fermentation reactor, avoiding 80% of the operating costs of prior art batch processing. The system runs continuously without stoppage or equipment or batch changes. The fermentation reactor optimizes the fermentation reaction to produce a constant biomass stream, full of oil-filled algae. The algaefaction process of the present invention is a unique and economical method to extract oil from the harvested algae. The fermentation reactor can be adjusted for any given set of operating conditions for a particular type of algae, and the present invention remains compatible with such alterations for continuous processing.

The foregoing disclosure and description of the invention is illustrative and explanatory thereof. Various changes in the details of the described method can be made within the scope of the appended claims without departing from the true spirit of the invention.

We claim:

1. An apparatus for fermentation of algae comprising:
    a gasifying means for converting a hydrocarbon composition into a syngas of a temperature range between 300° F. and 1500° F., said syngas being comprised of carbon monoxide, hydrogen and impurities;
    a pre-heating means for heating a biomass stream, said biomass stream being having of a liquid portion, a catalyst, and algal solids ranging between 15-92% by weight of said biomass stream, said biomass stream being pre-heated to a temperature range between 200° F. and 500° F.;
    a means for injecting said syngas and the pre-heated biomass stream as a mixture into a reactor;
    a means for separating the mixture into a gas component and a liquid component and an algal crude, said gas component being a lower temperature syngas, the means for separating comprising:
        a reactor suitable for housing said syngas and the pre-heated biomass stream at a temperature of greater than 600° F., said syngas being dissolved into said liquid portion of the biomass stream in said reactor and diffused into a cellular structure of the biomass stream for a predetermined amount of time; and
        a flashing means for changing the syngas-dissolved biomass stream from a liquid to a vapor within said cellular structure;
    collecting means for collecting the lower temperature syngas;
    a means for cycling said algal crude to the pre-heating means, the algal crude being cooled in order to pre-heat said biomass stream; and
    a means for collecting the cooled algal crude.
2. The apparatus of claim 1, further comprising:
    a means for recycling a portion of the algal crude into said gasifier.
3. The apparatus of claim 1, the mixture being pressurized between 500 and 2000 psig in said reactor.
4. The apparatus of claim 1, the reactor housing the mixture at a temperature of 1400° F.

5. The apparatus claim 1, said flashing means for depressurizing the diffused used biomass stream mixture in a flash chamber for less than 0.5 seconds so as to burst algal cell structures.

* * * * *